United States Patent [19]

Green

[11] Patent Number: 4,911,399

[45] Date of Patent: Mar. 27, 1990

[54] CAM VALVE FOR REGULATION OF FLUID FLOW THROUGH FLEXIBLE TUBING

[75] Inventor: Edward G. Green, Waukegan, Ill.

[73] Assignee: Anglo-American, Inc., Waukegan, Ill.

[21] Appl. No.: 361,973

[22] Filed: Jun. 6, 1989

[51] Int. Cl.$^4$ .............................................. F16K 7/04
[52] U.S. Cl. ............................................ 251/6; 251/4
[58] Field of Search .................................... 251/4, 6, 9

[56] References Cited

U.S. PATENT DOCUMENTS 3,289,999 12/1966 Konzak .
3,533,439 10/1970 Hall .
3,802,463 4/1974 Sobney .......................... 251/6 X
4,320,889 3/1982 Genese .
4,335,866 6/1982 Bujan .

Primary Examiner—John Fox
Attorney, Agent, or Firm—Neuman, Williams, Anderson & Olson

[57] ABSTRACT

A flow control device for regulating fluid flow through a length of flexible tubing comprising (a) a body assembly comprising a lower surface with a groove for supporting a length of flexible tubing, opposing side walls extending in the vertical plane along the longitudinal axis from the lower surface defining a passage for the tubing, a guide groove in one of the side walls, a rack gear positioned in the guide groove; (b) a rotatable cam assembly comprising a cam with an irregular radius which, at one position of rotation, extends into the passage, a pinion gear extending axially from and having the same center of rotation as the cam, wherein the pinion gear extends into the guide groove and operatively engages the rack gear; and (c) a cover connected to the top of the body assembly for retaining the pinion gear in operative engagement with the rack gear.

10 Claims, 2 Drawing Sheets

CAM VALVE FOR REGULATION OF FLUID FLOW THROUGH FLEXIBLE TUBING

FIELD OF THE INVENTION

This invention relates generally to flow control devices and more particularly to a cam valve to regulate fluid flow in flexible tubing.

BACKGROUND OF THE INVENTION

There are various roller clamp-type and other flow control devices which regulate fluid flow in flexible tubing. At present, these existing devices are used extensively in the pharmaceutical industry, principally to control the flow of intravenous solution into a patient's body. Although designed principally for pharmaceutical uses, these flow control devices also find application in other areas, for example, in laboratory experimentation, the photographic industry, and chemical processing.

In the assembly of existing devices, the manufacturer has often struggled with the problem of threading the flexible tubing through the device. This problem has been so severe that automated assembly of such devices in conjunction with flexible tubing is generally not possible. Thus, the production of existing devices has required human piecework assembly as a result of manually inserting the flexible tubing through the devices, a labor intensive task, which increases the cost of the valve. Moreover, the devices of the prior art do not provide for a positive means of regulating the flow of fluid through the flexible tubing. The devices of the prior art allow the flow setting to change if the device is touched or the flexible tubing is inadvertently jarred or tugged.

SUMMARY OF THE INVENTION

The present invention is intended to overcome the shortcomings of known devices by providing a flow control device which has an unrestricted path through the main body assembly allowing for easy insertion of flexible tubing in the production process. The present invention also provides a rotatable cam assembly comprising a cam with an irregular radius and a pinion gear extending from and having substantially the same center of rotation as the cam. The pinion gear engages a rack gear positioned in a guide groove in the body. This arrangement of body, cam, rack gear, and pinion gear allows the operator to exert less force when adjusting the device and also provides a more positive means of regulating the fluid flow through the flexible tubing.

The design of the device eliminates or greatly reduces the possibility that a desired flow rate will be changed by a sudden jarring of the device or by tugging or movement of the flexible tubing. In the case of regulating the flow of an intravenous solution into a patient's body, this feature is very important because an unwanted flow change can adversely affect the patient's condition.

The flow control device of the present invention generally comprises three parts: a body assembly, a rotatable cam assembly, and a cover. The body assembly, cam assembly and cover may all be injection molded plastic parts. In operation, the length of flexible tubing passes through the body of the device. The flow control device may advantageously be delivered from the manufacturer with the flexible tubing already automatically inserted through the body. If not, the flexible tubing may be inserted through the passage provided in the body of the device.

The body assembly of the flow control device comprises a lower surface for supporting a length of flexible tubing. The inventor has found that a substantially V-shaped groove is particularly advantageous in providing a supporting surface for the flexible tubing. The body is also comprised of opposing side walls extending in the vertical plane along the longitudinal axis from the lower surface and forming a passage for the flexible tubing. A guide groove is provided in at least one and preferably both of the side walls. A rack gear is positioned in the guide groove or grooves in the side walls. In one embodiment, opposing end walls extend in the vertical plane from the lower surface and define the ends of the side walls and body assembly.

The flow control device further comprises a rotatable cam assembly which comprises a cam with an irregular radius. The cam, at certain positions of rotation, extends into the passage in the body provided for the flexible tubing in order to engage and constrict the flexible tubing. A pinion gear or gears extend axially from the cam, with the teeth of the gear or gears extending in the radial direction. The pinion gears have substantially the same center of rotation as the cam, and extend into the guide grooves, with the teeth of the pinion gears engaging the rack gears in the guide grooves.

The cam is shaped in such a fashion that the cam has a irregular radius. The irregular radius of the cam causes the cam to engage and variably constrict the flexible tubing to various degrees, or to disengage the flexible tubing completely, depending upon the design of the cam and the position of rotation thereof. The passage in the body, the positioning of the guide grooves in the side walls and the shape of the cam may be designed so that at one position of rotation in the guide grooves the cam may not engage the flexible tubing and thus allow 100% fluid flow in the tubing. The rotation of the cam assembly brings the cam into increased engagement with the flexible tubing so that it increasingly causes constriction of the flexible tubing. The cam may be designed such that, at another position of rotation of the cam in the guide grooves, the cam sufficiently constricts the flexible tubing to completely restrict fluid flow.

The cam may be designed to permit any amount of constriction of the flexible tubing between 0 and 100 percent. Thus, the cam may be designed to allow flow to vary from 0 to 100 percent or, for example, may be designed to regulate flow from 25 to 50 percent of the capacity of the flexible tubing. If, as is common in pharmaceutical applications, the cam is designed to permit varying flow between 0 and 100 percent of the flexible tube's capacity, then at least at one position of the cam's rotation within the body, the cam does not constrict the flexible tubing at all and allows 100% flow through the flexible tubing. At another position of the cam's rotation within the body, the cam increases the constriction of the flexible tubing until the flow is completely shut off.

The flow control device further comprises a cover which is connected to the side walls and retains the pinion gear in operative connection with the rack gear. The cover may have a slot defined therein. In the preferred embodiment, the cam is designed so that the radius of the cam assembly is larger than the distance between the center of rotation and the top of the cover so that the cam assembly extends through the slot. If the cover is not of this construction, some other means for rotating the cam assembly must be provided, such as rotating an extension of the cam assembly which may protrude through a slot in a side wall.

Means are provided for retaining the cam assembly within the body. In one embodiment, opposing end walls accomplish this. In other embodiments this retention can be accomplished by the design of the cover or of the side grooves.

The operation of this device is extremely simple. The device may be operated by thumb pressure on the cam assembly which rotates the cam and pinon gear on the rack gear. As the cam assembly is rotated, the pinion gear advances down the rack gear, and the irregular radius of the cam allows the cam to variably engage the flexible tubing against the tube-supporting groove in the bottom of the body assembly, constricting the tubing and restricting or reducing the flow of fluid therein.

Generally, when beginning to use the device, the operator shuts the flow off by rotating the cam assembly over the flexible tubing to the closed position. The supply end of the tubing is then connected to a supply of fluid. The cam assembly is then rotated from the closed position to the appropriate position for the desired flow. When used in an intravenous system, once the air is discharged from the flexible tubing by the flow of fluid the discharge end of the flexible tubing can be connected to the intravenous system and the final adjustment for fluid flow can be made.

BRIEF DESCRIPTION OF THE DRAWINGS

For a more complete understanding of this invention, reference should be made to the embodiment illustrated in greater detail in the accompanying drawings and described below by way of an example of the invention.

DETAILED DESCRIPTION OF THE DRAWINGS

Figure 1:
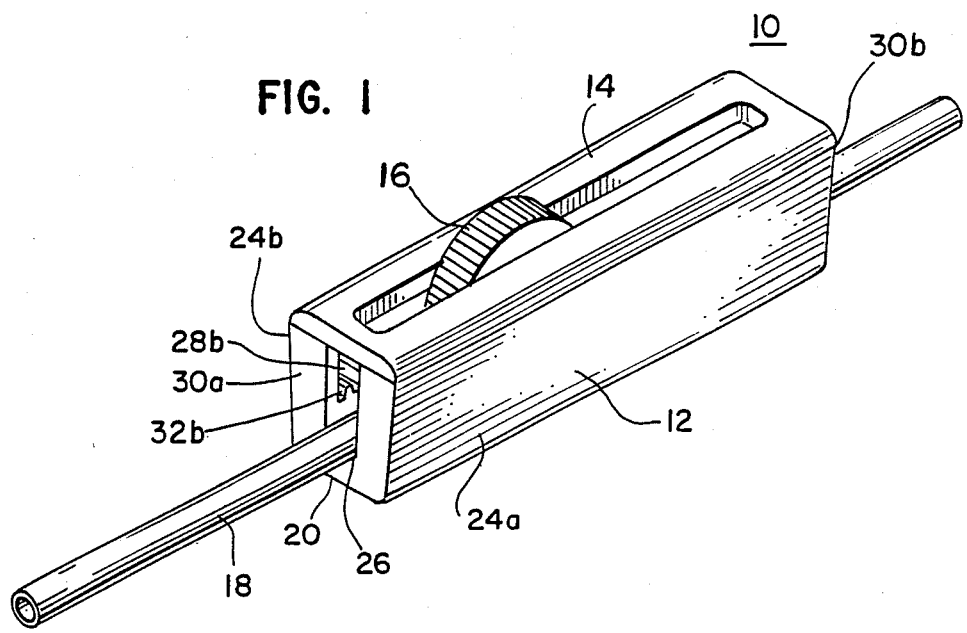
FIG. 1 is a perspective view of the flow control device of the present invention.

FIG. 1 shows the flow control device 10 of the present invention. As can be seen, the flow control device 10 generally comprises three parts: a body assembly 12, a cover 14, and a cam assembly 16. In use, a piece of flexible tubing 18 extends through the body assembly 12 with the cam assembly 16 engaging the flexible tubing 18 thereby having the capacity of wholly or partially constricting the flexible tubing, depending on the position of rotation of the cam assembly 16 in the body assembly 12, and the design of the cam assembly 16. The amount of constriction resulting from the interfering engagement of the cam assembly 16 on flexible tubing 18 alters the amount of fluid flow in the flexible tubing 18.

Figure 2:
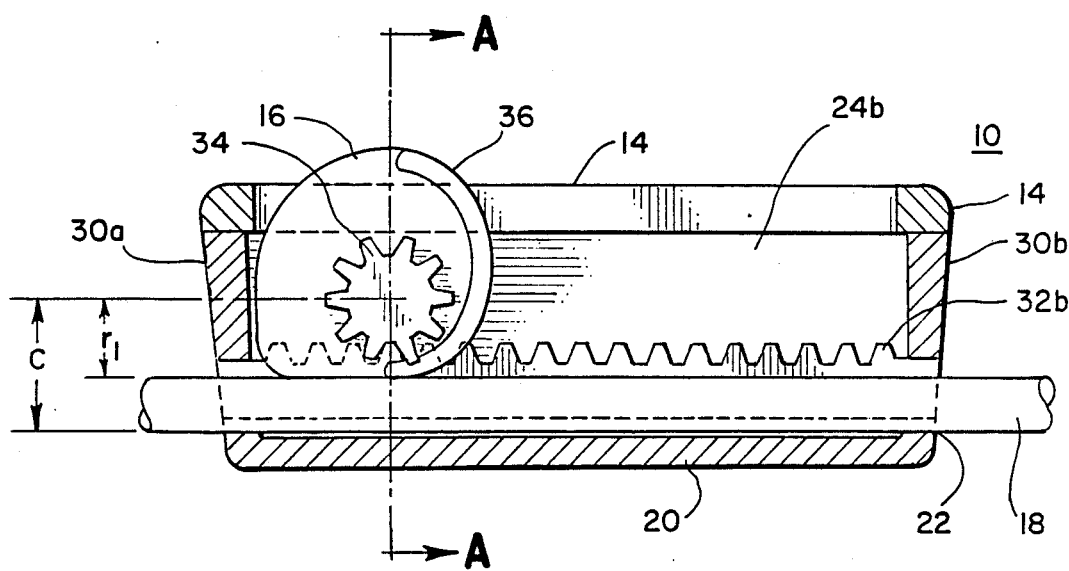
FIG. 2 is a schematic longitudinal sectional view of the flow control device showing the device in the open position.
Figure 3:
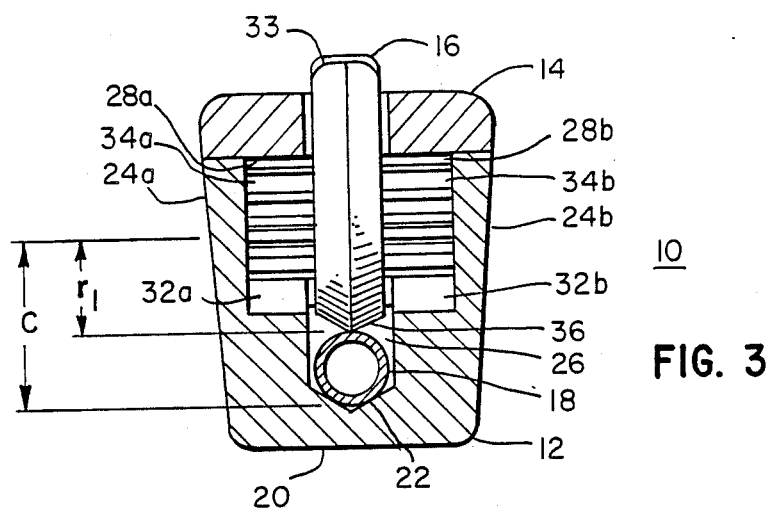
FIG. 3 is a schematic sectional view of the flow control device taken along the axial cross section line A—A of FIG. 2 showing the device in the open position.

As can be seen in greater detail in FIG. 2, the body assembly 12 has a lower surface 20, which as seen in FIG. 3 has a groove 22 molded into it for supporting flexible tubing 18. Preferably, the groove 22 is substantially V-shaped. The body assembly 12 further comprises opposing side walls 24a and 24b which extend in the vertical plane along the longitudinal axis from lower surface 20 and define a passage 26 for the flexible tubing 18. The side walls 24a and 24b have guide grooves 28a and 28b defined therein. FIG. 3 shows the preferred embodiment wherein both side walls 24a and 24b have guide grooves 28a and 28b defined therein. However, the invention may also be used with a guide groove 28 defined in only one of the two side walls 24.

Referring both to FIGS. 2 and 3, it can be seen that, in one embodiment, the opposing side walls 24a and 24b along with guide grooves 28a and 28b have their ends defined by opposing end walls 30a and 30b. As can be seen by referring to FIGS. 1 and 2 the end walls 30a and 30b define the ends of the body 12 and are preferentially substantially U-shaped thus defining an opening which is the continuation of passage 26 for allowing the flexible tubing 18 to pass through the body assembly 12. One purpose of the end walls 30a and 30b is to retain the cam assembly 16 within the device 10. The end walls 30 are not an essential element of the invention so long as the device 10 is constructed in a manner to retain cam assembly 16.

Referring to FIGS. 2 and 3, it can be seen that a rack gear 32b is positioned within at least one of the guide grooves 28b. In the preferred embodiment illustrated in the drawings, two rack gears 32a and 32b are provided. The rack gears 32a and 32b are respectively located in guide grooves 28a and 28b and extend longitudinally in the guide grooves.

Figure 4:
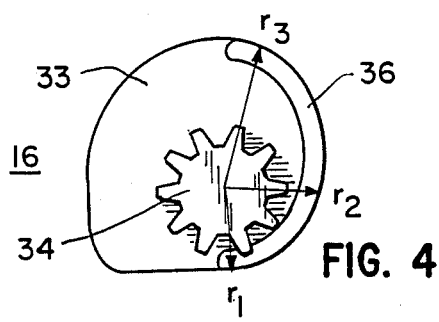
FIG. 4 is a side view of the cam assembly of the device.

The device further comprises a cam assembly 16. Referring to FIGS. 3 and 4, the cam assembly includes a cam 33 with an irregular radius. Extending axially from the cam 33 and operatively engaging the rack gears 32a and 32b are pinion gears 34a and 34b. As with the guide grooves 28a and 28b and the rack gears 32a and 32b, the preferred embodiment includes two pinion gears 34a and 34b. However, again as with the guide groove 28 and rack gear 32, the invention is operable with only one pinion gear 34. The pinion gears 34a and 34b have substantially the same center of rotation as cam 33 with the teeth of the gears extending in a radial direction. Each of these pinion gears 34a and 34b engage respectively one of the rack gears 32a and 32b.

As further seen in FIGS. 3 and 4, the cam 33 has an irregular radius. That is, cam 33 is designed so that it, at various points, has different radii, for example, $r_1$, $r_2$ and $r_3$. The irregular radius of cam 33 is designed so that when the cam assembly 16 is rotated, with the pinion gears 34a and 34b engaging the rack gears 32a and 32b, the cam 33 engages the flexible tubing 18 and constricts the flexible tubing 18 to varying degrees, depending on the rotational position and shape of the cam 33.

As seen most clearly in FIGS. 3 and 4, cam 33 has an edge surface 36 which engages and variably constricts the tubing 18. The shape of edge surface 36 is substantially the same as the shape of groove 22. Using this arrangement the cam surface 36 can engage and variably constrict the flexible tubing 18 so that the tubing is forced against the groove 22 in lower surface 20 thus allowing variation of the flow in the flexible tubing 18.

Figure 5:
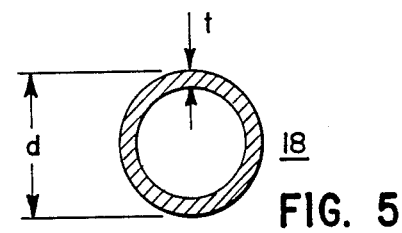
FIG. 5 is a sectional view of the flexible tubing of the device in the open position.

The flow can be varied from allowing 100% flow to completely terminating the flow of fluid through tube 18 or any percentage of flow in between depending on the design of the device 10 and especially the cam 33. FIG. 5 shows a cross section of flexible tubing 18 which has an outer diameter (d) and a wall thickness (t).

As seen in FIGS. 2 and 3, the cam assembly 16 is at one extreme of its rotation. As can be seen by reference to FIGS. 3 and 5, at this point in its rotation, the radius ($r_1$) of the cam 33, i.e. the distance from the center of rotation of the cam to the cam edge surface 36 which most closely comes into contact with the flexible tubing 18, when added to the outside diameter (d) of the flexible tubing, is less than or equal the distance (c) between the center of rotation of the cam assembly 16 and the bottom of the groove 22; that is, $r_1 + d \leq c$. As a result, the cam assembly 16 does not constrict the flexible tubing 18 and thus allows 100% flow capacity through the flexible tube 18. This position of rotation shall henceforth be referred to herein as the "open position."

Figure 6:
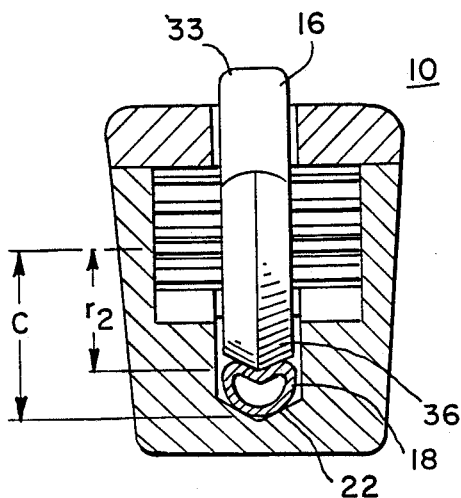
FIG. 6 is a schematic sectional view of the device along the axial cross section showing the device in a partially constricted position.

The irregular radius of the cam 33 can best be exemplified by describing the engagement of the edge surface 36 with the flexible tubing 18 as the cam assembly 16 is partially rotated. FIG. 6 shows the device 10 with the cam assembly 16 partially rotated so as to partially constrict, but not completely block, the flow of fluid in tube 18. Referring to FIGS. 5 and 6, the cam 33 is designed so that, in the partially rotated position, the radius ($r_2$) of the cam 33 in the partially rotated position exceeds the difference of the distance (c) between the center of rotation of the cam and the bottom of the groove 22 and the diameter (d) of the flexible tube 18; that is, $r_2 > c - d$, or $r_2 + d > c$. At the same time, however, in order to prevent complete constriction of the tube, the radius ($r_2$) of the cam 33 in the partially rotated position must be less than the difference between the distance (c) from the center of rotation of the cam assembly 16 to the bottom of the groove 22 and twice the thickness (2t) of the wall of the flexible tubing that is, $r_2 < c - 2t$, or $r_2 + 2t < c$. As a result, the cam edge surface 36 partially constricts the flexible tubing 18 thus restricting the flow of fluid through the tube. This is known as the "partially constricted position".

Figure 7:
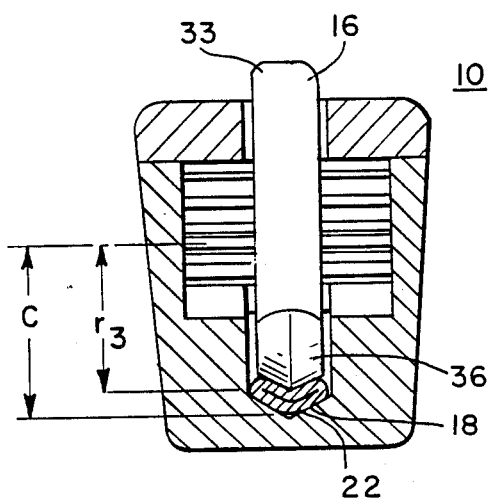
FIG. 7 is a schematic sectional view of the device along the axial cross section showing the device in the closed position.

At another position of rotation, seen in FIG. 7, the cam edge surface 36 may completely close the tube 18. Referring to FIGS. 5 and 7, at this position of rotation, the radius ($r_3$) of the cam 33, when added to twice the thickness (2t) of the wall of the flexible tubing 18, is approximately equal to the distance (c) from the center of rotation of the cam assembly 16 to the bottom of the groove 22; that is, $r_3 + 2t = c$. Thus, the flexible tube is completely constricted, and the flow of fluid therein is prevented. This position of rotation shall be referred to as the "closed position."

Thus, the rotation of cam assembly 16 regulates the fluid flow in tube 18. As is readily apparent from the foregoing description, the flow of fluid can be regulated by designing the cam 33 to permit fluid flow in any amount between 0 to 100 percent.

Referring to FIGS. 1 and 3, cover 14 is connected to the top of side walls 24a and 24b or the end walls 30a and 30b defining the top of the guide grooves 28a and 28b and retaining the pinion gears 34a and 34b in operative engagement with the rack gears 32a and 32b. In a preferred embodiment, the cover 14 is ultrasonically welded to the side walls 24a and 24b and end walls 30a and 30b thus assuring that pinion gears 34a and 34b will not lose operative engagement with the rack gears 32a and 32b.

Because at one position of its rotation, the open position, the cam edge surface 36 does not extend substantially into passage 26, it is possible to easily insert flexible tubing 18 through the passage 26. Indeed the flow control device 10 of the present invention allows this assembly operation to be performed by machine rather than by hand, as is common in many present flow restriction devices.

Referring to FIGS. 1, 2, and 3, the device 10 is operated by rotating the cam assembly 16, as with pressure by the thumb of the operator's hand, which causes the cam 33, and thereby the pinion gears 34a and 34b to move along the rack gears 32a and 32b. The interaction of pinion gears 34a and 34b with rack gears 32a and 32b allows for a positive means of controlling and maintaining the rotation of the cam assembly 16, resulting in more positive metering of the flow through the tubing 18. Moreover when the cam assembly 16 is set at the desired location, the engagement of pinion gears 34a and 34b with rack gears 32a and 32b renders it virtually impossible to change the flow by a sudden jarring of the device 10 or by tugging on the tubing 18.

The figures depict the preferred embodiment of the device 10 wherein the cover 14 defines a slot extending through the cover and into the interior of the body assembly 12. The cam 33 is designed so that the radius of the cam 33 at all positions is larger than the distance between the center of rotation of the cam assembly 16 and the top of the cover 14. Thus, the cam 33 extends through the slot in the cover 14. The cam assembly 16 can then be rotated by thumb pressure on the cam 33. The slot depicted also provides the means for retaining cam assembly 16 in body assembly 12. In other embodiments, the cover 14 could be designed without a slot. In such a design, the cam assembly 16 could be rotated by applying a rotational force to cam assembly by alternate means, such as by rotating an extension of the cam assembly which may protrude through a slot in a side wall 24.

The device 10, in one embodiment, is provided with flexible tubing 18 already extending through passage 26. The device 10 may be operated by moving the cam assembly 16 to the closed position whereby flow is completely restricted in the tubing 18. The supply end of tubing 18 is then connected to a supply of fluid. The cam assembly 16 may be rotated to a position which allows the desired amount of flow through the tubing 18. In an embodiment where the device 10 is used for an intravenous system, after the connection of a fluid source to the flexible tubing 18, the cam assembly is rotated to allow flow through the tubing thereby pushing any air out of the tubing. At this point the discharge end of the tubing 18 can be connected to the intravenous system and the cam assembly 16 may be rotated so that the desired flow is achieved.

From the above description it is apparent that the objects of the present invention have been achieved. While only certain embodiments have been set forth, alternative embodiments and various modifications will be apparent from the above description to those skilled in the art. For example, while in the preferred embodiment the device of the present invention is used with intravenous systems for patients, the present device also finds applicability in the laboratory or other uses. These and other alternatives are considered equivalents and within the spirit and scope of the present invention. Having described the invention, what is claimed is:

I claim:

1. A flow control device for regulating fluid flow through a length of flexible tubing comprising:
   (a) a body assembly comprising:
      a lower surface with a tube-supporting groove for supporting a length of flexible tubing;
      opposing side walls extending in the vertical plane along the longitudinal axis from said lower surface defining a passage for said tubing;
      a guide groove in one of said side walls;
      a rack gear positioned in said guide groove;
   (b) a rotatable cam assembly comprising:
      a cam with an irregular radius which, at one position of rotation, extends into said passage;
      a pinion gear extending axially from and having substantially the same center of rotation as said cam, wherein said pinion gear extends into said guide groove and operatively engages said rack gear;
   (c) a cover connected to the top of said body assembly for retaining said pinion gear in operative engagement with said rack gear.

2. The flow control device of claim 1 wherein said cam has an irregular radius such that rotation of said cam assembly variably extends said cam into said passage and into engagement with said flexible tubing in such a way that the variable extension of the cam into said passage variably constricts said flexible tubing.

3. The flow control device of claim 2 wherein: (a) said cover defines a slot extending through said cover and into the interior of said body assembly; and (b) said cam assembly extends through said slot in said cover at every position of rotation.

4. The flow control device of claim 2 wherein said tube-supporting groove is substantially V-shaped in cross section.

5. The flow control device of claim 4 wherein the edge of said cam which comes into operational engagement with said flexible tubing is substantially V-shaped in cross section.

6. The flow control device of claim 2 wherein said cam, at one position of rotation of the cam assembly, does not come into operational engagement with the flexible tubing.

7. The flow control device of claim 6 wherein said cam is of a substantially eccentric shape.

8. The flow control device of claim 2 wherein said cam, at one position of rotation of the cam assembly, extends into said passage for the flexible tubing and into operational engagement with said flexible tubing in such a way that the flow in said tubing is partially restricted.

9. The flow control device of claim 2 wherein said cam, at one position of rotation of the cam assembly, extends into said passage for the flexible tubing and into operational engagement with said flexible tubing in such a way that flow in said tubing is totally restricted.

10. The flow control device of any one of claims 1–9, further comprising a length of flexible tubing positioned in said passage.

* * * * *